United States Patent [19]

Hestermann et al.

[11] 4,073,810
[45] Feb. 14, 1978

[54] PRODUCTION OF ORGANOPHOSPHINES

[75] Inventors: Klaus Hestermann, Erftstadt Bliesheim; Bernd Lippsmeier, Hurth-Knapsack; Gero Heymer, Erftstadt Liblar, all of Germany

[73] Assignee: Hoechst Aktiengesellschaft, Frankfurt am Main, Germany

[21] Appl. No.: 549,172

[22] Filed: Feb. 12, 1975

[30] Foreign Application Priority Data

Feb. 16, 1974 Germany .............................. 2407461

[51] Int. Cl.² ............................. C07F 9/50; C07F 9/54
[52] U.S. Cl. ....................... 260/606.5 P; 260/606.5 F
[58] Field of Search ................... 260/606.5 P, 606.5 F

[56] References Cited

U.S. PATENT DOCUMENTS

| 3,030,421 | 4/1962 | Reuter et al. | 260/606.5 P |
|---|---|---|---|
| 3,316,293 | 4/1967 | Carr et al. | 260/606.5 F |
| 3,389,183 | 6/1968 | Harp | 260/606.5 P |
| 3,755,460 | 8/1973 | Staendeke | 260/606.5 F |
| 3,760,001 | 9/1973 | Staendeke | 260/606.5 P |
| 3,855,311 | 12/1974 | Staendeke | 260/606.5 P |

OTHER PUBLICATIONS

Kosolopoff Organophosphorus Compounds, Wiley--Interscience, N.Y., V1, pp. 7, 8, 24, 25, 37–40 (1972).
Kosolopoff, Organophosphorus Compounds, Wiley--Interscience, N. Y. V2, pp. 192–194 (1972).
Henderson et al., JACS, vol. 82, p0p. 5794–5800 (1960).
Kosolapoff et al., Organic Phosphorus Compounds, John Wiley & Sons, Inc., N.Y., vol. 1, 1972, pp. 10, 16, 21, 22, 30.

Primary Examiner—Helen M. S. Sneed
Attorney, Agent, or Firm—Connolly and Hutz

[57] ABSTRACT

Production of organophosphines of the general formula $R_nPH_{3-n}$, in which R stands for identical or different, substituted or unsubstituted alkyl, cycloalkyl or aralkyl groups having from 1 to 18 carbon atoms, preferably from 1 to 4 carbon atoms, more preferably from 1 to 2 carbon atoms, and $n$ stands for a whole number within the range 1 and 3. The compounds are more particularly produced by continuously reacting hydrocarbon halides of the general formula RX, in which R has the meaning given hereinabove and X stands for halogen, especially for chlorine or bromine, with hydrogen phosphide, and primary or secondary organophosphines at temperatures within the range 100° and 600° C and under pressures of up to 20 atmospheres in contact with a catalyst being placed in a reactor. Gaseous matter issuing from the reactor is cooled and the resulting organophosphonium halides $(R_nPH_{4-n})X$ are hydrolyzed in conventional manner to the corresponding organophosphines.

18 Claims, No Drawings

PRODUCTION OF ORGANOPHOSPHINES

The present invention relates to a process for making organophosphines of the general formula $R_nPH_{3-n}$, in which R stands for identical or different, substituted or unsubstituted alkyl, cycloalkyl or aralkyl groups having from 1 to 18 carbon atoms, preferably from 1 to 4 carbon atoms, more preferably from 1 to 2 carbon atoms, and n stands for a whole number within the range 1 and 3.

A. W. Hoffmann (cf. Chem. Ber. 4, 605 (1871)) was the first to describe the preparation of alkylphosphines by reacting alkyl iodides RI with phosphonium iodide in the presence of Zno:

$$2 RI + 2PH_4I + ZnO \rightarrow 2 RPH_2 \cdot HI + ZnI_2 + H_2O$$

This process is not satisfactory, however as expensive iodides are required to be used as starting materials therein. In addition to this, it is necessary for the reaction to be effected batchwise under pressure, in closed reactors.

Alkylphosphines can also be made by reacting alkylhalides with alkali metal or alkaline earth metal phosphides (cf. U.S. Pat. No. 2,437,797 and R. I. Wagner, A. B. Burg, J.Am.Soc. 75, 3869 (1953)). In this process, it is necessary to first prepare in a separate operation and in liquid ammonia, the alkali metal or alkaline earth metal phosphide by adding elementary alkali metal or alkaline earth metal, which is difficult to handle.

A further process described more recently comprises reacting hydrocarbon halides with a $PH_3 \cdot AlCl_3$ complex (cf. F. Pass, E. Steininger, H. Zorn, Monatsb. Chem. 93 230 [1962] and German Patent "Auslegeschrift 1 126 867"). Here again, it is neccesary to first prepare in a separate operation the $AlCl_3$-complex of $PH_3$. The process is further handicapped by the loss of $AlCl_3$.

Reducing alkylhalogenophosphines with $LiAlH_4$ is a route which has often been tried for making alkylphosphines, in the laboratory (G. M. Kosolapoff, L. Meier, Organic Phosphorus Compounds, Wiley-Interscience, vol. 1,4 [1972]).

This process, wherein difficulty accessible alkylhalogenophosphines and very expensive $LiAlH_4$ are the starting materials, cannot be used for the commercial production of organophosphines, for reasons of economy.

The present invention now unexpectedly provides a process for making organophosphines of the general formula $R_nPH_{3-n}$, in which R stands for identical or different, substituted or unsubstituted alkyl, cycloalkyl or aralkyl groups having from 1 to 18 carbon atoms, preferably from 1 to 4 carbon atoms, more preferably from 1 to 2 carbon atoms, and n stands for whole number within the range 1 and 3, which comprises continuously reacting starting materials selected from hydrocarbon halides of the general formula RX, in which R has the meaning given hereinabove and X stands for halogen, especially for chlorine or bromine, with hydrogen phosphide, primary or secondary organophosphines at temperatures within the range 100° and 600° C and under pressures of up to 20 atmospheres in contact with a catalyst being placed in a reactor; cooling gaseous matter issuing from the reactor; and hydrolyzing in conventional manner the resulting organophosphonium halides $(R_nPH_{4-n})X$ so as to obtain the corresponding organophosphines.

The process should preferably be carried out with the use of at least 0.1 mol of hydrocarbon halide per mol of hydrogen phosphide or phosphine. It is also advantageous for the reaction to be effected at atmospheric pressure. The starting material should preferably be passed over the catalyst at the speed necessary to provide for a contact period within the range 0.1 and 60 seconds. It is also advantageous for the starting materials to be mixed together, for the mixture to be heated to about 150° C and for the mixture so heated to be passed over the catalyst. The starting materials are more generally reacted in contact with the catalyst at temperatures within the range 200° and 350° C. The reaction itself may be effected in a solid bed or flow bed reactor.

Active carbon, especially active carbon having a BET-surface area of more than 10 m²/g, is particularly well adapted for use as a catalyst. It is good practice to employ the active carbon in the form of particles having a size between 1 and 10 mm, for use in a solid bed reactor, and to employ pulverulent active carbon, for use in a flow bed reactor. Further useful catalysts include finely dispersed metals belonging to the first or eight subgroup of the Periodic System of the elements, which may be used alone or in combination, e.g. gold, platinum or palladium. It is possible for these metals to be deposited on a carrier being inert under the reaction conditions, such as $Al_2O_3$ or $SiO_2$, for example.

The gases coming from the reactor can be cooled as desired, commonly down to a temperature of about 20° C. This may be achieved in stages so as to effect the separation of the phosphines and phosphonium halides, respectively. Those gases which remain uncondensed during cooling, should be scrubbed with an acid, preferably with aqueous hydrochloric acid, and thereby freed from the organophosphines which are obtained in the form of the corresponding organophosphonium compounds. By increasing the pH of the acid solutions of the organophosphonium compounds with the aid of basic substances, preferably with the use of an aqueous base, it is possible to hydrolyze the organophosphonium compounds and to liberate the organophosphines. The starting materials which are passed through the reactor and remain unreacted therein should conveniently be recycled.

The reactions which occur in the reactor are believed to be based on the following empirical formulae:

$$RCl + PH_3 \rightarrow [RPH_3]^+ Cl^- \rightleftarrows RPH_2 + HCl$$

$$RCl + RPH_2 \rightarrow [R_2PH_2]^+ Cl^- \rightleftarrows R_2PH + HCl$$

$$RCl + R_2PH \rightarrow [R_3PH]^+ Cl^- \rightleftarrows R_3P + HCl$$

As results, it is possible to produce predominantly the mono- or di- or triorganophosphines, depending on the particular alkyl chloride/hydrogen phosphide or organophosphine-ratio selected in the reaction mixture.

The contact time of the reaction mixture with the catalyst naturally influences the total conversion to organophosphines and the proportionate share of mono-, di- and triorganophosphines in the total conversion, relatively large proportions of di- and triorganophosphines being obtained for long contact times.

As regards hydrogen phosphide or organophosphines, it is possible for those substances to be used in admixture with $CO_2$, $N_2$, HCl or steam, for example, or in admixture with further gases being inert with respect to the reaction mixture.

As reported above, the uncondensed gas coming from the reactor is scrubbed with an acid with the resultant formation of an acid organophosphonium salt solution, from which unreacted gaseous hydrogen phosphide is allowed to escape. Unconsumed hydrocarbon halide also escapes therefrom, provided that it is in gas form under the reaction conditions selected. Liquid hydrocarbon halides are separated from the aqueous acid organophosphonium salt solution, as a second liquid phase.

Unreacted starting material passing through the acid solution should conveniently be recycled to the reactor.

As a result of the different basicity of primary, secondary and tertiary phosphines, it is possible for the individual phosphines to be separated from each other as early as during the hydrolysis of the acid organophosphonium salt solutions, by gradually increasing their pH values.

The process of the present invention, which is naturally not limited to the embodiments specifically described herein, enables, for example, organophosphines to be produced continuously in commercial quantities from readily accessible halides RX and hydrogen phosphide $PH_3$, which is the simplest phosphine and a by-product being obtained in commercial quantities, e.g. in the production of sodium hypophosphite. The organophosphines produced in accordance with the present invention are important starting materials for making flameproofing agents, pharmaceutical preparations etc.

EXAMPLE 1

The methylphosphines $CH_3PH_2$, $(CH_3)_2PH$ and $(CH_3)P$ were produced. To this end, a mixture of 25 l of $PH_3$/h and 25 l of $CH_3Cl$/h was placed in a preheater and continuously preheated therein to 150° C over a period of 5 days. After that period, the mixture so preheated was passed at 280° C and at atmospheric pressure through a solid bed reactor having an active carbon catalyst placed therein (particle size: about 2.5 mm; BET-surface area: about 1400 m$^2$/g) and contacted therewith for 17 seconds. The hot reaction gases consisting of $CH_3PH_2$, $(CH_3)_2PH$, $(CH_3)_3P$ coming from the reactor, HCl and unreacted $PH_3$ and $CH_3Cl$ were introduced into a container maintained at a temperature of 60° C to effect the condensation of the following organophosphonium salts consisting substantially of $(CH_3)_2PH \cdot HCl$ and $(CH_3)_3P \cdot HCl$ together with relatively minor proportions of $(CH_3)PH_2 \cdot HCl$. The uncondensed gas mixture which had a temperature of 60° C, was delivered to a scrubbing tower in which concentrated hydrochloric acid was circulated by means of a pump and in which the gas mixture was freed from residual proportions of $(CH_3)_2PH$ and $(CH_3)_3P$, and from $CH_3PH_2$ as the principal reaction product, which were all obtained in the form of organophosphonium chlorides.

Unreacted $PH_3$ and $CH_3Cl$ fractions coming from the scrubbing tower were recycled to the reactor.

Once the concentrated hydrochloric acid solution in the scrubbing tower was found to contain sufficient organophosphonium chloride, it was removed and replaced by fresh concentrated hydrochloric acid, without arresting the reaction.

The hydrochloric acid solution, which substantially contained monomethylphosphonium chloride, was diluted with $H_2O$ and monomethylphosphine $CH_3PH_2$ having a purity of more than 99 % was recovered therefrom in known manner. The residual hydrochloric acid solution was admixed with aqueous NaOH until it had a pH-value of 12, and 1.5 weight % of a mixture of $(CH_3)_2PH$ and $(CH_3)_3P$, based on $CH_3PH_2$, was obtained, which was distilled off from the aqueous solution.

The liquid phase of methylphosphonium chlorides, which was condensed at 60° C, was admixed gradually with an aqueous NaOH-solution. 7 parts of $CH_3PH_2$ were initially recovered therefrom and then 72 parts of $(CH_3)_2PH$ and 21 parts of $(CH_3)_3P$.

The quantities of $(CH_3)_2PH$ and $(CH_3)_3P$ so obtained were united with the quantities recovered from the aqueous hydrochloric acid and separated distillatively.

Altogether 5036 g of $PH_3$ gave 5332 g of $CH_3PH_2$, 248 g of $(CH_3)_2PH$ and 85 g of $(CH_3)_3P$. The initial $PH_3/CH_3Cl$-gas mixture was converted as follows, in a single pass reaction: 25 % $PH_3$ to $CH_3PH_2$; 0.8 % of $PH_3$ to $(CH_3)_2PH$ and 0.25 % of $PH_3$ to $(CH_3)_3P$.

EXAMPLE 2

$PH_3$ and $CH_3Cl$ were used in the molar ratio of 1:1 and contacted at 200° C and atmospheric pressure over a period of 15 seconds with the active carbon catalyst used in Example 1. The other conditions were the same as those used in that Example. The following result was obtained for a single pass reaction of the starting gas mixture: 218 g of $PH_3$ gave 12 g of $CH_3PH_2$. This corresponded to a conversion of 3 %. $(CH_3)_2PH$ and $(CH_3)_3P$ could be identified in traces only.

EXAMPLE 3

$PH_3$ and $CH_3Cl$ were used in the molar ratio of 1:1 and contacted for 10 seconds at 325° C at atmospheric pressure with the active carbon catalyst of Example 1. The other conditions were the same as those used in that Example. The following results were obtained for a single pass reaction of the starting gas mixture: 305 g of $PH_3$ gave 125 g of $CH_3PH_2$ (29 % $PH_3$ conversion), 28 g of $(CH_3)_2PH$ (5 % $PH_3$ conversion) and 10 g of $(CH_3)_3P$ (1.4 % $PH_3$ conversion).

EXAMPLE 4

$PH_3$ and $CH_3Cl$ were used in the molar ratio of 1:2 and contacted for 18 seconds at 275° C at atmospheric pressure with the active carbon catalyst of Example 1. The other conditions were the same as those used in that Example. The following results were obtained for a single pass reaction of the starting gas mixture: 260 g of $PH_3$ gave 102 g of $CH_3PH_2$ (28 % $PH_3$ conversion) 21 g of $(CH_3)_2PH$ (4.4 % $PH_3$ conversion) and 7.5 g of $(CH_3)_3P$ (1.3 % $PH_3$ conversion).

EXAMPLE 5

$PH_3$ and $CH_3Cl$ were used in the molar ratio of 1:10 and contacted for 19 seconds at 275° C and under an overpressure of 2 mm of water with the active carbon catalyst of Example 1. The other conditions were the same as those used in that Example. The following results were obtained for a single pass reaction of the starting gas mixture: 134 g of $PH_3$ gave 1 g of $CH_3PH_2$ (0.5 % $PH_3$ conversion), 39 g of $(CH_3)_2PH$ (16% $PH_3$ conversion) and 18 g of $(CH_3)_3P$ (6% $PH_3$ conversion).

EXAMPLE 6

$CH_3PH_2$ and $CH_3Cl$ were used in the molar ratio of 1:2 and contacted for 15 seconds at 260° C at atmospheric pressure with the active carbon catalyst of Example 1. The other conditions were the same as those used in that Example. The following results were obtained for a single pass reaction of the starting gas mixture: 107 g of $CH_3PH_2$ gave 9.8 g of $(CH_3)_2PH$ (7.1 % of $CH_3PH_2$ conversion) and 3.2 g of $(CH_3)_3P$ (1.9 % of $CH_3PH_2$ conversion), 96 % of unreacted $CH_3PH_2$ was recovered.

EXAMPLE 7

$PH_3$ and $C_2H_5Br$ were used in the molar ratio of 1:1 and contacted for 5 seconds at 250° C at atmospheric pressure with the active carbon catalyst of Example 1. The other conditions were the same as those used in that Example. The following result was obtained for a single pass reaction of the starting gas mixture: 212 g of $PH_3$ gave 11 g of $C_2H_5PH_2$ (2.8 % of $PH_3$-conversion).

EXAMPLE 8

$PH_3$ and $CH_3Cl$ were used in the molar ratio of 1:1 and contacted for 5 seconds at 350° C at atmospheric pressure with a platinum catalyst. The platinum was finely divided material deposited on an $Al_2O_3$-carrier. The other conditions were the same as those used in Example 1. The following results were obtained for a single pass reaction of the starting gas mixture: 100 g of $PH_3$ gave 7 g of $CH_3PH_2$ (4.7 % of $PH_3$ conversion) and minor quantities of $(CH_3)_2PH$ and $(CH_3)_3P$.

EXAMPLE 9

Gold metal deposited on an $SiO_2$-carrier was used as the catalyst under the conditions described in Example 8. The following result was obtained for a single pass reaction of the starting gas mixture: 100 g of $PH_3$ gave 4 g of $CH_3PH_2$ (2.7 % of $PH_3$ conversion). $(CH_3)_2PH$ and $(CH_3)_3P$ were identified in traces.

EXAMPLE 10

Finely divided palladium deposited on a $SiO_2$-carrier was used as the catalyst under the conditions described in Example 8. Tthe following result was obtained for a single pass reaction of the starting gas mixture: 149 g of $PH_3$ gave 17.9 g of $CH_3PH_2$ (8.5 % of $PH_3$ conversion) and minor amounts of $(CH_3)_2PH$ and $(CH_3)_3P$.

EXAMPLE 11

$PH_3$ and $CH_3Cl$ were used in the molar ratio of 1:1 and contacted for 40 seconds at 280° C at atmospheric pressure with the active carbon catalyst of Example 1. The other conditions were the same as those used in that Example. The following results were obtained for a single pass reaction of the starting gas mixture: 240 g of $PH_3$ gave 170 g of $CH_3PH_2$ (50.2 % of $PH_3$ conversion), 44 g of $(CH_3)_2PH$ (10.1 % of $PH_3$ conversion) and 6 g of $(CH_3)_3P$ (1.1 % of $PH_3$ conversion).

EXAMPLE 12

$PH_3$ and $CH_3Cl$ were used in the molar rato of 1:1 and contacted for 30 seconds at 280° C at atmospheric pressure with the active carbon catalyst of Example 1. The active carbon used in the present Example consisted of particles with a size within the range 0.5 and 1 mm. The other conditions were the same as those used in Example 1. The following results were obtained for a single pass reaction of the starting gas mixture: 250 g of $PH_3$ gave 230 g of $CH_3PH_2$ (65.2% of $PH_3$ conversion). 55 g of $(CH_3)_2PH$ (12.1 % of $PH_3$ conversion) and 11 g of $(CH_3)_3P$ (2 % of $PH_3$ conversion).

We claim:

1. In the process for making organophosphines of the formula $R_nPH_{3-n}$, in which R is alkyl having from 1 to 4 carbon atoms, and $n$ is a whole numnber of 1 to 3, the improvement which comprises continuously reacting hydrogen phosphide as starting material with alkyl halide of the formula RX, in which R has the meaning given hereinabove and X is chlorine or bromine, at temperatures of 100° to 600° C within a gas atmosphere inert to the reaction mixture and under pressure of up to 20 atmospheres in contact with a catalyst in a reactor for a period within the range 0.1 and 60 seconds wherein the catalyst is selected from the group consisting of active carbon, a finely divided metal from the first or eighth subgroup of the Periodic System of the elements and blends of such metals; cooling gaseous matter issuing from the reactor; and hydrolyzing the resulting organophosphonium halides $(R_nPH_{4-n})X$ to the corresponding organophosphines.

2. The process as claimed in claim 1, wherein at least 0.1 mol of hydrocarbon halide is used per mol of the said hydrogen phosphide.

3. The process as claimed in claim 1, wherein the reaction is effected at atmospheric pressure.

4. The process as claimed in claim 1, wherein the starting materials are mixed together, heated to about 150° C and the mixture is contacted with the catalyst.

5. The process as claimed in claim 1, wherein the starting materials are reacted in contact with the catalyst at temperatures within the range 200° and 350° C.

6. The process as claimed in claim 1, wherein the reaction is effected in a solid bed reactor.

7. The process as claimed in claim 1, wherein the reaction is effected in a flow bed reactor.

8. The process as claimed in claim 1, wherein the active carbon catalyst has a BET-surface area of more than 10 m²/g.

9. The process as claimed in claim 1, wherein the active carbon catalyst has a particle size within the range 1 and 10 mm.

10. The process as claimed in claim 7, wherein pulverulent active carbon is used as the catalyst.

11. The process as claimed in claim 1, wherein the metal is gold, platinum or palladium.

12. The process as claimed in claim 1, wherein the metal is deposited on a carrier.

13. The process as claimed in claim 12, wherein the carrier is $Al_2O_3$ or $SiO_2$.

14. The process as claimed in claim 1, wherein the gaseous matter coming from the reactor is cooled stagewise down to about 20° C.

15. The process as claimed in claim 1, wherein the gaseous matter issuing from the reactor and remaining uncondensed during cooling is scrubbed with an acid with the resultant formation of the corresponding organophosphonium compounds.

16. The process as claimed in claim 15, wherein the acid is aqueous hydrochloric acid.

17. The process as claimed in claim 15, wherein the pH value of the resulting aqueous solutions of the organophosphonium compounds is increased by means of a basic substance to the extent necessary to hydrolyze the organophosphonium compounds and to liberate the organophosphines.

18. The process as claimed in claim 17, wherein the basic substance is an aqueous base.

* * * * *